United States Patent [19]
Graves et al.

[11] Patent Number: 6,125,689
[45] Date of Patent: Oct. 3, 2000

[54] NON-DESTRUCTIVE SEMICONDUCTOR WAFER TEST SYSTEM

[75] Inventors: Clinton Graves, Danville; Clinton Graves, II, San Francisco, both of Calif.

[73] Assignee: Graves' Trust Group, Danville, Calif.

[21] Appl. No.: 09/124,159

[22] Filed: Jul. 28, 1998

Related U.S. Application Data

[60] Provisional application No. 60/055,934, Aug. 15, 1997.

[51] Int. Cl.⁷ .............................. B01D 15/08; G01N 30/08
[52] U.S. Cl. .................... 73/23.37; 73/23.41; 73/19.02; 422/89; 95/87; 96/101; 436/161
[58] Field of Search ................................ 73/23.37, 23.41, 73/19.02, 864.81; 118/725, 750; 422/89, 83; 96/106, 101; 95/102, 87; 436/161, 177–178, 157

[56] References Cited

U.S. PATENT DOCUMENTS

| | | | |
|---|---|---|---|
| 3,179,499 | 4/1965 | Hampton | 23/253 |
| 4,698,486 | 10/1987 | Sheets | 250/492.2 |
| 4,982,089 | 1/1991 | Johnson | 250/304 |
| 5,012,052 | 4/1991 | Hayes | 250/288 |
| 5,092,218 | 3/1992 | Fine et al. | 86/50 |
| 5,106,756 | 4/1992 | Zaromb | 436/161 |
| 5,152,176 | 10/1992 | Bryselbout et al. | 72/23.41 |
| 5,174,149 | 12/1992 | Grob et al. | 73/23.41 |
| 5,174,881 | 12/1992 | Iwasaki et al. | 204/298.25 |
| 5,407,867 | 4/1995 | Iwasaki et al. | 437/228 |
| 5,435,169 | 7/1995 | Mitra | 73/23.41 |
| 5,522,918 | 6/1996 | Shiramizu | 95/87 |
| 5,547,497 | 8/1996 | Klemp et al. | 96/104 |
| 5,563,352 | 10/1996 | Helmig | 73/863.12 |
| 5,665,314 | 9/1997 | Berger et al. | 422/89 |
| 5,725,664 | 3/1998 | Nanbu et al. | 118/52 |
| 5,872,306 | 2/1999 | Arnold | 73/23.37 |
| 5,918,257 | 6/1999 | Mifsud et al. | 73/23.34 |
| 5,962,774 | 10/1999 | Mowry et al. | 73/23.37 |
| 5,996,420 | 12/1999 | Lee | 73/864.81 |

OTHER PUBLICATIONS

Lakeman, Steven, "Contamination Control in PVD Cluster Tools Through Mass Spectrometry", Semiconductor International, Oct. 1996, pp. 114–119.

Product Brochure from Finningan Corporation, GCQ GC/MS System/GCQ *Tandem* GC/MS/MS System.

*Primary Examiner*—Hezron Williams
*Assistant Examiner*—David J. Wiggins
*Attorney, Agent, or Firm*—Townsend and Townsend and Crew LLP

[57] ABSTRACT

The invention provides methods and systems for identifying compounds released from a semi-conductor wafer. Compounds are released from the wafer by subjecting the wafer to a rapid temperature excursion in a very low pressure chamber. The released compounds are often isolated using gas chromatography. Diffusion between the layers of a multiple layer semi-conductor structure can be minimized by directly heating a target surface of the wafer using radiant heating.

32 Claims, 7 Drawing Sheets

NON-DESTRUCTIVE SEMICONDUCTOR WAFER TEST SYSTEM

CROSS-REFERENCE TO RELATED APPLICATIONS

This application claims the benefit of priority from U.S. Provisional Patent Application Ser. No. 60/055,934, filed Aug. 15, 1997, the full disclosure of which is incorporated herein by reference.

BACKGROUND OF THE INVENTION

1. Field of the Invention

The present invention relates generally to semiconductor processing and test equipment, and more particularly to a method and system for identifying semiconductor fabrication contaminants by subjecting wafers to temperature excursions at a low pressure, and by analyzing the compounds which are released using gas chromatography and/or mass spectrometry.

Semiconductor wafers are highly sensitive to contaminants introduced into the wafer structure during fabrication. As the processes involved in fabrication can be highly complex, it is desirable to specifically identify any sources of contamination during fabrication, rather than searching for contaminants after fabrication is complete and the finished semi-conductor devices fail to perform as desired.

Recently, mass spectrometers have been used to test for contaminants within deposition chambers. Mass spectrometers are particularly well adapted for sensing and quantifying a limited number of atomic or molecular compounds. For example, mass spectrometers now sense $H_2$, $H_2O$, $N_2$, $O_2$ and $CH_x$ present in plasma vapor deposition chambers. Hence, by attaching a mass spectrometer to the evacuated plasma deposition chambers, the spectrometer can detect vacuum leaks as unacceptable amounts of nitrogen, oxygen, or water in the process chamber environment. Additionally, mass spectrometers may be able monitor for a few known contaminants within a semi-conductor process chamber, such as contaminants from photo-resist residue and the like.

Unfortunately, identifying an unknown contaminant from an unknown contamination source remains problematic. Often, the specific compound causing contamination or failure of the semi-conductor device is not known. Semi-conductor devices are being built with more and more layers having a wide variety of layer materials, and the interaction of all of the compounds to which the wafer is exposed can be difficult to predict. In an attempt to provide a mechanism for identifying contaminants, it has recently been proposed to heat small pieces of the completed wafer in an evacuated chamber. The temperature is increased in a series of steps, with mass spectrometry being applied at each step to quantify a few atomic species or simple compounds which are released by the wafer at each temperature. By studying the relative amounts of these target species which are released over time, the make-up of the contaminating compound can sometimes be derived. This process is called "trending".

Trending suffers from several distinct disadvantages. First, the wafer is destroyed in the testing process, both by being broken into small pieces, and by heating at a number of elevated temperatures for a significant amount of time. Second, trending can only indicate a limited number of contaminant compounds, and only where the composition of those compounds is known before the test is initiated. As the contaminants themselves are often broken into atomic or simple molecular substructures, precise identification of a complex or unknown compound is difficult and/or impossible. Trending also requires skilled analysts having a knowledge of the contaminant compounds, including their boiling points, their disassociation pathways, and the like. Even for these specialists, it can be difficult to determine the specific contaminant species. For example, when monitoring the quantity of hydrogen released at various temperatures, it can be difficult to determine whether the hydrogen is released from water, a complex photo-resist, or any of thousands of other compounds. Where more than one contaminant compound is present, identification of each compound using the trending process is particularly problematic.

For the above reasons, it would be desirable to provide improved methods and systems for testing of semi-conductor wafers. Preferably, such systems and methods would allow identification and quantification of compounds and contaminants, even where the presence of the compound is not suspected. It would be ideal to provide non-destructive wafer test methods for monitoring wafer quality without decreasing the total quantity of wafers produced.

2. Description of the Background Art

U.S. Pat. No. 5,152,176, describes a process and apparatus for determining the quantity of impurities in a gas by chromatography in a gas phase. U.S. Pat. No. 5,522,918, describes a method for analyzing organic substances within a clean room by sub-cooling a semi-conductor substrate to trap volatile organic substances on the substrate.

SUMMARY OF THE INVENTION

The present invention provides methods and automated systems for identifying compounds, particularly contaminants, released from a semi-conductor wafer. Generally, the compounds are released from the wafer by subjecting the wafer to a rapid temperature excursion in a very low pressure chamber. The released compounds are often isolated using gas chromatography, so that the mass spectra of the individual compounds can be compared to one of the commercially available mass spectra libraries. These libraries can contain the spectra of 126,000 or more compounds, allowing the identification of contaminants which are not even known to be present. Advantageously, diffusion between the layers of a multiple layer semi-conductor structure can be minimized by directly heating a target surface of the wafer using radiant heating. In some embodiments, gas chromatography is selectively used in a non-destructive quality assurance program which also includes tandem mass spectrometry (sometimes called mass spectrometry/mass spectrometry). Such a quality assurance program can specifically identify potential contaminants, can provide quantitative information on the amount of the contaminate compounds present on the wafers, and can monitor any increase or decrease in the amount of contaminants, all without substantially disrupting the fabrication process or waiting until the finished semi-conductor devices fail.

In a first aspect, the present invention provides a method for testing semi-conductor wafers. The method comprises heating the wafer in an evacuated chamber to release one or more compounds from the wafer. A gas sample is collected from the evacuated chamber, the sample including the released compounds. The sample is introduced into a gas chromatograph to a identify the released compounds.

Typically, the pressure of the sample will be increased after collection and before introduction into the gas chromatograph. Ideally, the heating step is terminated prior to substantial diffusion between the layers of the wafer, to avoid degradation of the wafer's electrical properties. This method allows identification of contaminants from a single sample collected at a single temperature, without requiring destruction of the wafer.

In another aspect, the present invention provides a non-destructive method for detecting contaminants of semi-conductor wafers. The method comprises heating at least a portion of the wafer in an evacuated chamber to a target temperature, so that one or more contaminant compounds are released by the wafer. A gas sample is collected from the evacuated chamber, the sample including the released compounds. The heating is terminated, and the wafer is cooled to minimize diffusion between a plurality of layers of the wafer. This avoids degradation of the electrical properties across these adjacent layers. A pressure of the sample is increased, and the sample is introduced into a gas chromatograph or a tandem mass spectrometer to identify the released compounds.

In yet another aspect, the present invention provides a system for testing semi-conductor wafers. The system comprises walls defining a vacuum chamber for holding a wafer. A heat source raises the temperature of the wafer within the chamber, and a sample collection system draws a gas sample from within the chamber and passes the sample to a gas chromatograph or a tandem mass spectrometer. To increase the pressure of the gas sample for chromatography, the gas collection system may comprise a cooled container which cryopumps the sample when the chamber is evacuated. Conveniently, this container will often be isolatable from the chamber so that raising the temperature of the container increases the pressure of the sample for identification of the compounds within the sample.

DETAILED DESCRIPTION OF THE SPECIFIC EMBODIMENTS

The present invention provides systems and methods for identifying compounds released from a target surface of semi-conductor wafers or other structures. The present invention is particularly well adapted for use with multi-layer semi-conductor thin film structures, and can automatically identify and quantify contaminants of these complex thin film structures, often without significantly degrading the electrical properties of the semi-conductor devices which are being tested.

The systems and methods of the present invention will allow a semi-skilled operator, having only a fundamental understanding of chemistry and instrumentation, to qualitatively and quantitatively identify volatile compounds which are present on the wafer. Through specific identification of the compounds, likely sources of wafer contamination can be readily identified. Hence, the present invention will find application in a wide variety of semi-conductor processes and fabrication environments, allowing ready identification of photo-resist residue, solvents, and other sources of contamination. The present invention will find its most immediate application within a quality assurance regimen for semi-conductor fabrication processes. As the exact composition and quantity of compounds can be provided, even at very low concentration levels, the identification and elimination of sources of contamination will be greatly facilitated, even before contamination leads to degradation of the semi-conductor devices.

Figure 1:
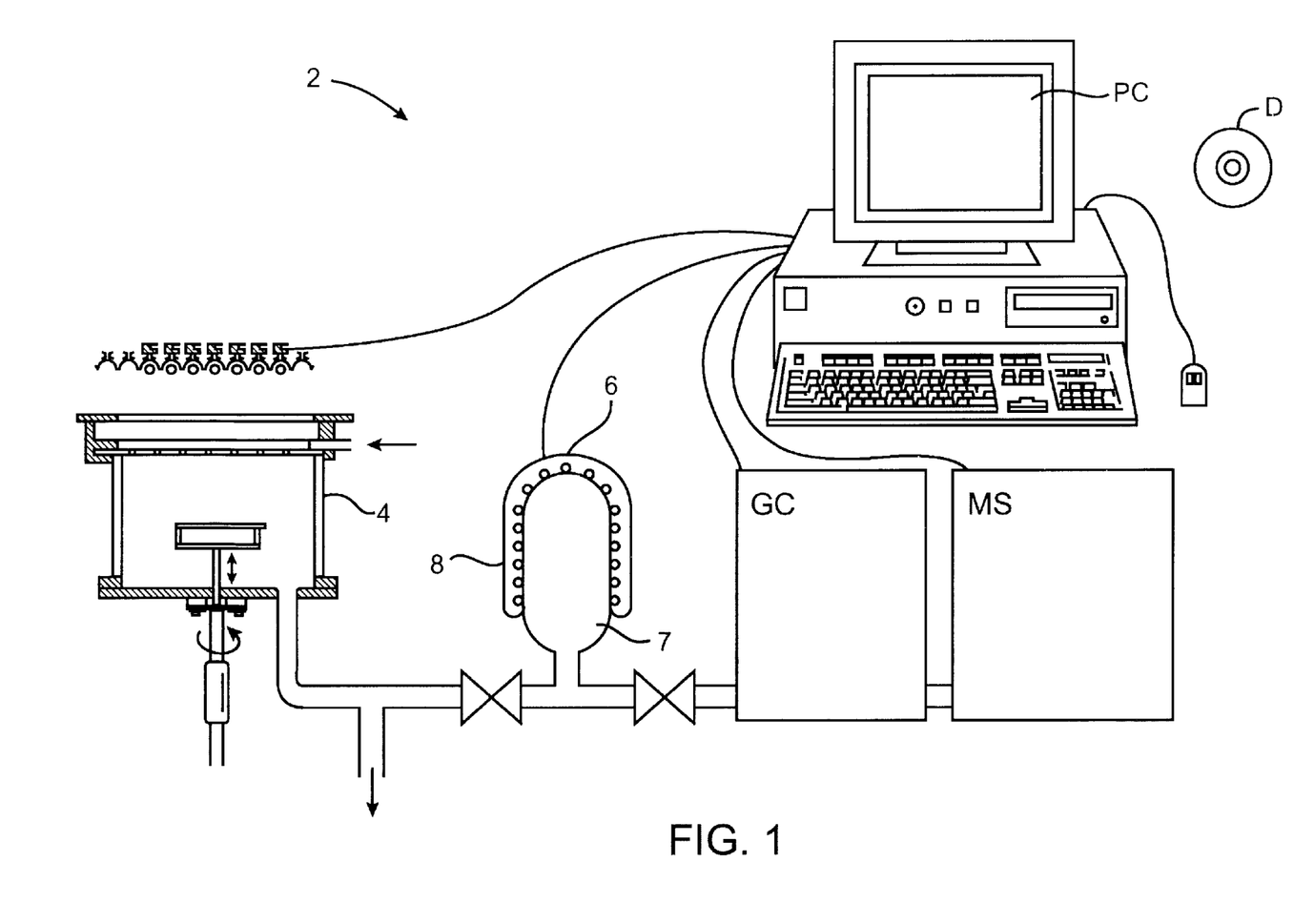
FIG. 1 is a schematic view of a non-destructive wafer contaminant test system, in which a gas sample is collected from a wafer while the wafer is subjected to a rapid and controlled temperature excursion, and in which the gas sample pressure is increased for gas chromatography and mass spectrometry, according to the principles of the present invention.

Referring now to FIG. 1, a non-destructive wafer test system 2 includes a rapid temperature excursion system 4 and a gas sample collection and pressurization system 6. Pressurized samples from the temperature excursion system, which will include compounds boiled off of the wafer, will be injected into gas chromatograph GC, which separates the released compounds from each other, and from any carrier gas used for their transport. The separated compounds can then be analyzed in a mass spectrometer MS, which preferably has tandem mass spectrometer capabilities. Preferably, a personal computer PC controls the temperature excursion, sample collection, pressurization, and the gas chromatography and mass spectroscopy within non-destructive test system 2, and automatically analyzes the data provided by the test system for identification and quantification of contaminants. A computer program embodying the method of the present invention will typically be transferred to the personal computer PC from a disk D, which may comprise an optical disk, a magnetic recording disk, or the like. Alternatively, such software may be transferred over a computer network such as the Internet.

The operation and structure of rapid temperature excursion system 4 is similar to a low temperature epitaxial growth system described in co-pending U.S. patent application Ser. No. 08/795,498, filed Feb. 5, 1997, (Attorney Docket No. 16918-000300), the full disclosure of which is incorporated herein by reference. As used within non-destructive test system 2, rapid temperature excursion system 4 makes use of radiant heating to directly raise the temperature of a target surface of the semi-conductor wafer. The wafer is suspended within a chamber of the temperature excursion system, using a stand which is transparent to the radiant energy, so that the effective thermal mass of the wafer is minimized. The walls of the chamber will often be cooled, and the back surface of the wafer opposite the target surface will be exposed to the cooled walls during heating. Hence, the target surface will generally be at a higher temperature than other portions of the wafer structure.

Prior to heating of the wafer, the atmosphere within rapid temperature excursion system 4 will generally be reduced to quite low levels, generally to a pressure below $10^{-4}$ Torr, ideally to a pressure of about $10^{-8}$ Torr. This will facilitate the release of volatile compounds from the wafer, particularly when the temperature of the wafer is elevated.

The temperature excursion system directly heats the target surface with radiant energy having a frequency spectrum for which the target surface is at least partially opaque. By directing such radiant energy with sufficient intensity flux at the target surface, the target surface is heated rapidly to the desired processing temperature. This provides a rapid heat excursion, in which the target surface is quickly raised to the pre-determined processing temperature, is maintained at that temperature for only the minimum time required to collect the gas sample, and then cools immediately when radiant heating is terminated.

Multi-layer semi-conductor structures generally make use of differing electrical properties of adjacent film layers. Semi-conductor devices generally benefit from thin layer structures having well defined boundaries. Unfortunately, dopants and other compounds which differentiate these boundary layers are susceptible to diffusion across the boundaries at elevated temperatures. By allowing the substrate material in film layers underlying the target surface to remain at more hospitable temperatures, the system and method of the present invention minimize diffusion between these underlying layers. Additionally, the use of direct radiant heating allows the target surface to be quickly and controllably raised to the predetermined target temperature (particularly to temperatures of about 1,000° C. or less, which is sufficient for boiling of most volatile semi-conductor contaminants), to maintain that temperature for as short a time as is required, and to then be cooled by heat transfer from the heated target surface to the surrounding chamber and to the remainder of the wafer structure itself, thereby minimizing the diffusion time.

Temperature excursion system 4 also provides a particularly advantageous gas flow over the target surface for heating of the wafer, and also for collection of the gases released by the target surface. Specifically, the carrier gas is injected into a plenum disposed between the radiant heater and the wafer. The plenum, which is preferably formed of a material which is transparent to the radiant energy, directs the air smoothly downward toward the target surface of the wafer, optionally providing a laminar or creeping laminar flow over the target surface. In some embodiments, this laminar flow will provide an efficient and even heating over the target surface. Alternatively, the axial position of the wafer within the temperature excursion system may be altered, or the speed of rotation of the wafer may be increased to provide a turbulent flow over the wafer surface. This will enhance transportation of released compounds away from the target surface of the wafer, and prevents their reattachment or reaction with other wafer materials.

While the wafer is at the target elevated temperature, and optionally during the temperature ramp-up and/or ramp-down, a sample of the carrier gas and any compounds released by the wafer will be stored in container 7. As described above, the temperature excursion chamber will preferably be at very low pressures. Gas chromatographs benefit from much higher pressures, the gas chromatograph column injection pressure often being significantly more than atmospheric pressure. Often times, the sample is collected by cryopumping the sample from the evacuated test chamber. Once the sample has been collected, a valve between the test chamber and the container is closed. Cooling of the container is terminated, and in some embodiments, the container is heated to increase the pressure of the gas sample.

Once the gas sample within container 7 is adequately pressurized, a valve separating pressurization and collection system 6 from the gas chromatograph GC is opened. The gas chromatograph will separate the compounds within the sample, typically making use of a separating column having a solid phase absorptive material. Generally, the gas chromatograph and mass spectrometer will operate in conjunction, so that the mass spectra of the separated compounds are scanned numerous times over a test period. This allows the individual mass spectra of the compounds separated by the column to be compared with any of the commercially available spectra libraries, which can include the spectra of 126,000 or more compounds. Advantageously, the personal computer PC can compare the scanned mass spectra with the library automatically, so that compounds released by the wafer may be identified, even where the presence of those compounds was not suspected.

Although the separation of compounds using gas chromatograph GC and the subsequent identification of the separated compounds using mass spectrometer MS is highly advantageous, this analysis process may require 20 minutes or more for completion. Those of skill in the art will recognize that such a time consuming quality assurance test may be incompatible with testing of each and every wafer during production. Hence, the gas chromatograph/mass spectrometry analysis will often be performed only on selected wafers during production. As semi-conductor wafers are produced in relatively consistent batches, selective testing for contamination should provide reliable information on new compounds present on other wafers of the same batch.

To ensure that the level of contamination present within a batch does not vary, it will often be desirable to perform mass spectra analysis of gas samples without separating the sample into individual compounds. This can be performed in less time than a gas chromatography and mass spectroscopy analysis. To enhance the detection of specific contaminants which are suspected to be present within an unseparated gas sample (often including contaminants which have previously been identified using gas chromatograph GC), the mass spectrometer MS will preferably have tandem mass spectroscopy capabilities, often called "mass spectroscopy/mass spectroscopy."

A particular advantageous integrated gas chromatography/mass spectroscopy system, including a personal computer and software for analysis of gas samples, is commercially available from Finnigan Corporation of San Jose, Calif., under the trademark GCQ™.

Figure 1A:
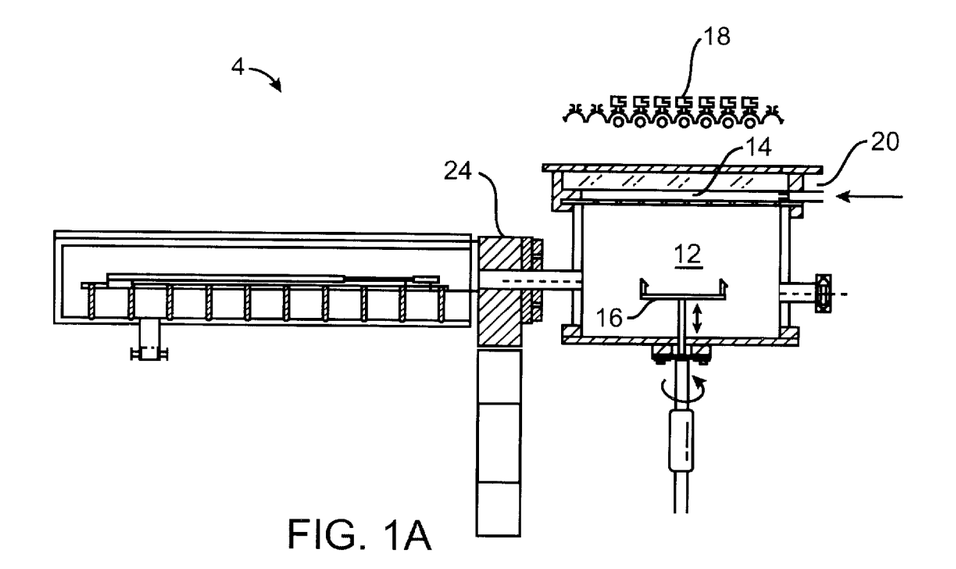
FIG. 1A is a cross-sectional side view of an exemplary rapid temperature excursion system for use in the non-destructive test system of FIG. 1, in which a target surface of a wafer is directly and evenly heated by a bank of heat lamps while the wafer is rotatably and translatably suspended in the chamber.
Figure 1B:
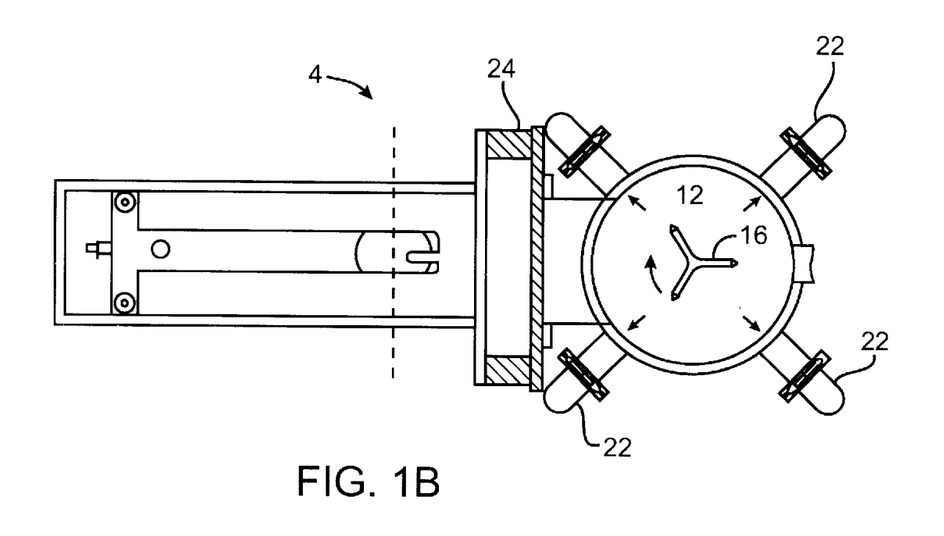
FIG. 1B is a top view of the temperature excursion system of FIG. 1A, showing the gas sample collection ports, and also showing a wafer handling system.

Referring now to FIGS. 1A and B, an exemplary rapid temperature excursion system 4 includes a test chamber 12 and a plenum 14. A substrate support 16 is axially translatable and rotatable within the test chamber as shown. A radiant heater 18, preferably comprising a bank of parallel heat lamps, directs radiant energy through the plenum structure and into the deposition chamber. A carrier gas will be provided through at least one source gas inlet port 20 into plenum 14, and will preferably be evacuated from below the support structure using sample collection ports 22.

Wafers are introduced and removed from the test chamber through a valve 24, preferably with a manipulator arm having a single axis of movement, taking advantage of the rotational and translational capabilities of the substrate support structure to load and unload the wafers. Those of skill in the art will recognize that a wide variety of alternative wafer handling mechanisms might be provided.

Figure 2:
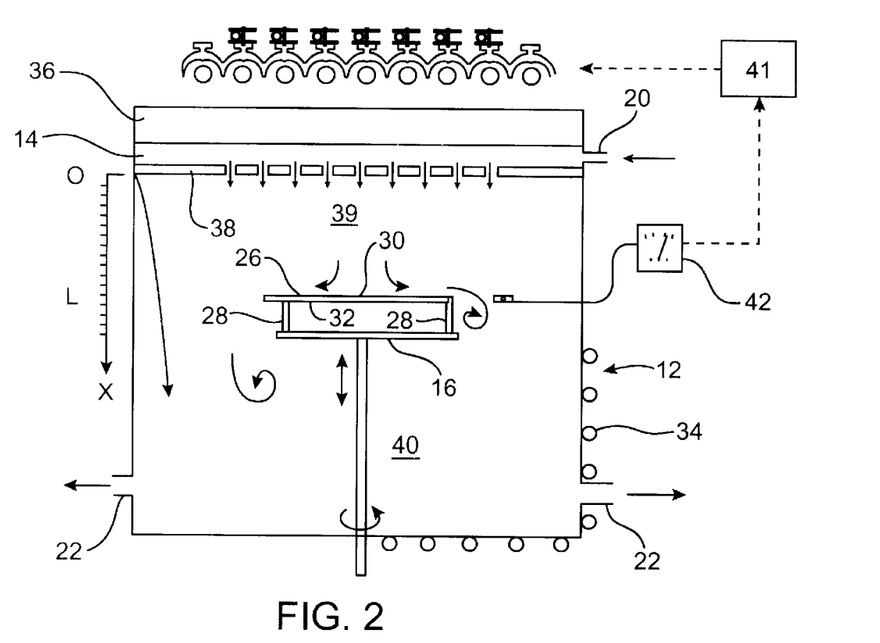
FIG. 2 is a schematic illustration of the temperature excursion chamber of the system of FIG. 1A, illustrating the gas flow dynamics and direct heating arrangement.

The rapid temperature excursions and advantageous gas flow dynamics of the deposition chamber will be explained with reference to FIG. 2. A wafer 26 is supported by support structure 16 on three quartz pins 28. A target surface 30 of the wafer is oriented towards radiant heater 18, while a back surface of the wafer 32 is substantially thermally exposed to the chamber and walls. As the walls are cooled with a coolant system 34, heat from the back side of the wafer will be radiated during testing, and may also be dissipated by convection.

The carrier gas which enters the test system through inlet port 20 will initially enter plenum 14. Advantageously, the plenum distributes the carrier gas with a laminar flow toward the target surface of the wafer, and also transmits the radiant energy from radiant heater 18 in substantially the same direction as the carrier gas flow. To provide these capabilities, plenum 14 includes a thick outer structural wall 36 comprising a material which is transparent to the radiant energy. As test processes will often be performed at quite low pressures, wall 36 will preferably have considerable structural strength. To effectively transmit the radiant energy, wall 36 will often comprise quartz, ideally being between about 1.0 and 4.0 inches in thickness.

A perforate barrier 38 is disposed between the plenum and the test chamber. The perforations are sized and located to provide a smooth laminar flow of the carrier gas towards the substrate, and will also pass the radiant energy towards the target surface. Generally, perforate barrier 38 will also comprise a material which is transparent to the radiant energy, ideally also comprising quartz. As the pressure loads on perforate barrier 38 will be considerably less than on outer wall 36, it will typically be considerably thinner than that structure. It should be understood that while only a single carrier gas inlet port is illustrated, a number of ports may be provided to evenly distribute the gas throughout the plenum, the gas ideally being introduced into the plenum from a gas distribution ring disposed around the plenum.

As described above, the wafer will preferably be axially translatable within the test chamber system towards the radiant heater. The wafer's position (transverse to the flow of carrier gas) within the test chamber effectively separates the chamber into a gas supply portion 39 and a gas removal portion 40. By axially translating the wafer, an effective length L of the gas supply portion of the test chamber can be varied with the axial position of the wafer X. This will allow the effective aspect ratio (length divided by diameter) of the chamber to be tailored.

By altering the gas flow and aspect ratio, it may be possible to provide a turbulent flow over the target surface of the wafer, if such turbulence is desired to enhance removal of released compounds, of the like. Rotation of the wafer within the chamber ensures even heating from the parallel bank of heat lamps, and may also be used to tailor the flow of the carrier gas over the target surface. The flow characteristics of the chamber are more fully explained in co-pending U.S. patent application Ser. No. 08/795,498, filed Feb. 5, 1997 (Attorney Docket No. 16918-000300), the full disclosure of which has previously been incorporated herein by reference.

Once the carrier gas, together with any compounds released by the active surface, flows beyond the wafer 26, the flow will often become substantially turbulent. The evacuation portion 40 of the test chamber need not be adapted to try to maintain laminar flow, and the system may in fact benefit from the turbulence. Specifically, turbulent flow under the back surface 32 of wafer 26 may increase convective cooling of that surface, and may simplify the removal of evacuation gases through evacuation system 22 without distorting the pressure distribution over the target surface. Nonetheless, a plurality of radial outlet ports may help minimize any radial distortion in pressures.

A temperature sensor system 42 allows the temperature of the wafer to be monitored and controlled throughout the test process. Temperature signals from temperature sensor system 42 will be processed by feedback control circuitry 41, and may be used to control radiant heater 18, the height of substrate support 16, and other process variables to provide the desired temperature at the target surface for the desired process time. This feedback system may be integrated into or controlled by the personal computer PC of FIG. 1.

Figure 3A:
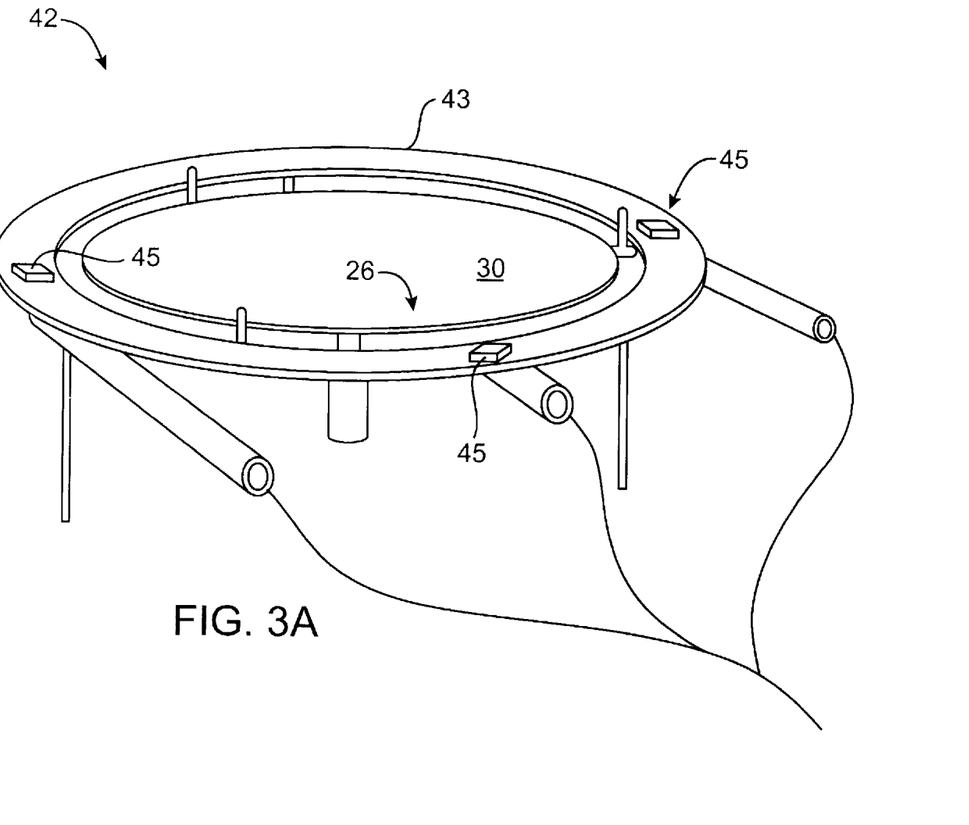
FIGS. 3A and B illustrate a preferred wafer temperature monitoring system for use with the temperature excursion chamber of FIG. 1A.
Figure 3B:
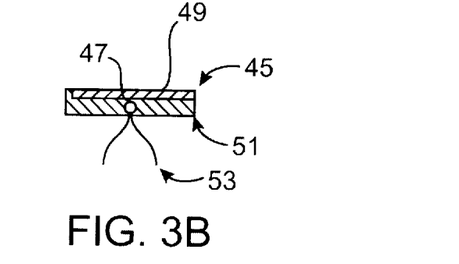

A preferred temperature sensor structure is illustrated in FIGS. 3A and B. A quartz stand 43 supports at least one silicon chip 45 having a thermocouple 47. In the embodiment shown, the thermocouple is mounted between a silicon cover 49 and an etched silicon backplate 51. Thermocouple wires 53 couple the thermocouple (ideally being a type K thermocouple) to the feedback circuitry. By mounting the silicon chips adjacent the perimeter of wafer 26 substantially even with target surface 30, the radiant heating of the silicon chips will be substantially equivalent to that of the wafer. Alternative thermocouple support structures may similarly be used to model different substrate structures, and stand 43 may optionally be adjustable in height to accommodate different axial positions of the wafer.

Figure 3C:
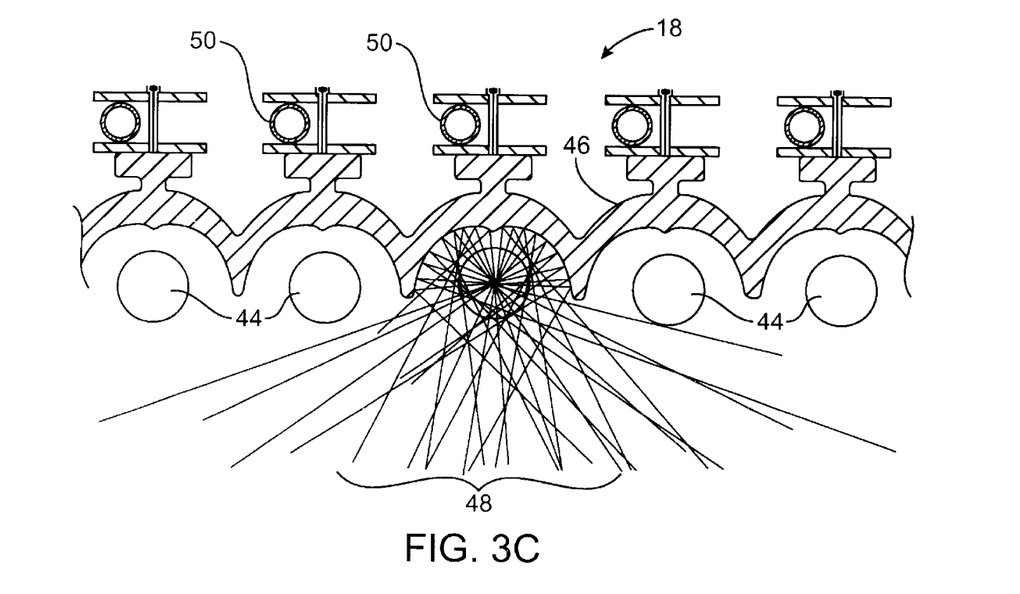
FIG. 3C is a detailed view of a particularly advantageous parallel radiant heating lamp bank and reflector structure for use with the temperature excursion chamber of FIG. 1A.

A preferred arrangement for radiant heater 18 is shown in more detail in FIG. 3. Lamps 44 will typically be longer than the diameter of the target surface, and will be arranged in a parallel bank beneath a reflector 46. The lamps will ideally provide radiant energy 48 having a frequency spectrum which passes efficiently through the material of the plenum, and which is absorbed by the target surface of the wafer. In other words, the wafer will preferably be opaque to the radiant energy, whereas the quartz or other material of the plenum will be transparent to that same radiant energy. In the exemplary embodiment, seven halogen lamps of 1500 watts each are included in radiant heater 18. These lamps are commercially available from the Ushio Corporation as part number J240-1500WB. These exemplary lamps have a color temperature of 3400° K, and provide a substantial output of radiant heat energy with a wavelength below 1.2 $\mu$m. Reasonable heat transfer estimations can be make by assuming that silicon has an emissivity of 0.39 wavelengths below 1.2 $\mu$m, and an emissivity of 0.0 for all other wavelengths.

Reflector 46 includes a double concave reflective surface which helps to columnate the radiant energy and distribute it evenly in the spaces between the lamps. Even heating of the target surface is further enhanced by rotating of the wafer, as is described above. Radiant heater 18 is cooled by a cooling system, ideally comprising copper tubing associated with each lamp, as shown.

Figure 4:
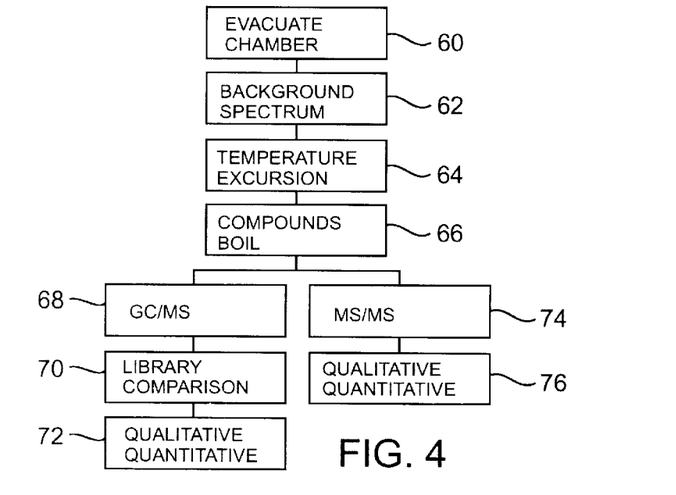
FIG. 4 illustrates a preferred method for identifying and/or quantifying wafer contaminants, according to the principles of the present invention.

A method for operating non-destructive test system 2 of FIG. 1 will be described with reference to FIG. 4. Generally, the operation of this test system will be highly automated, with the individual operations largely controlled by the personal computer, per input or programming by the operator.

As described above, the wafer will often be placed into the test chamber using automated wafer handling equipment. While the rapid temperature excursion system and chamber will optionally be used solely for testing for contaminants and other compounds, it should be recognized that additional semi-conductor processes may alternatively take place within this system. For example, the direct radiant heating and gas flow of the exemplary rapid temperature excursion system 4 is particularly advantageous for growth of epitaxial film layers. Hence, in some embodiments, the present methods may be incorporated into other wafer fabrication steps, rather than requiring a separate stand-alone testing system.

Wafer handling is preferably fully automated, and is ideally a cassette-to-cassette system, thereby facilitating integrating the test system and method into known wafer fabrication techniques. In some embodiments, each wafer of a batch of wafers within a cassette will be tested. Alternatively, only a select wafer or wafers from each cassette, or only one or more wafers from a group of cassettes will be selectively tested.

Once the wafer is placed in the chamber and the chamber is sealed, the chamber is evacuated to a fairly low pressure, preferably below about $10^{-4}$ Torr, and ideally to about $10^{-8}$ Torr. Typically, mechanical pumps and/or cryogenic high vacuum pumps are used to evacuate the chamber 60.

Optionally, carrier gas having a simple and well defined mass spectra is introduced into the chamber to displace any atmospheric gases surrounding the wafer. This helps prevent confusion between the atmospheric gases and the compounds released by the wafer during the test. Preferably, the carrier gas comprises a non-reactive gas such as helium or the like.

Once the chamber is evacuated, a background spectrum 62 is optionally obtained to identify and quantify compounds present in the test sample which have sources other than the sample wafer. In some embodiments, such a background spectra can be obtained without pressurizing the background spectra sample by introducing the low pressure sample to the mass spectrometer. In alternative embodiments, the pressure of the background sample may be raised to isolate individual compounds using a combination of gas chromatography and mass spectroscopy. In some embodiments, the background spectrum will only be obtained for selected wafers of a batch, depending on the particulars of the quality assurance regimen.

Heating of the target surface of the test wafer is preferably initiated by powering up the radiant heater. The increase in surface temperature of the wafer can be controlled by the power provided to the radiant heater. The direct radiant heating system of the present invention is capable of heating the target surface to 800° C. in as little as 1.4 seconds or less, with the target temperature typically being below about 1,000° C. Similarly, it will generally be desired to minimize both test temperatures and the time that the wafer is heated, so long as sufficient amounts of the contaminants or other compounds are released during temperature excursion 64.

The release of the contaminants and other compounds from the target surface of the wafer will generally be provided by boiling of the compounds 66 within the low pressure, high temperature environment of the test chamber. The compounds present on the wafer will often boil at different temperatures, and samples may optionally be taken at a series of different temperatures to help isolate the individual compounds. However, obtaining such independent samples may increase the time the wafers is subjected to the elevated test temperatures. Therefore, only a single sample will preferably be taken, and the individual compounds will be separated by the gas chromatograph.

It should be noted that this single sample can provide a significantly greater amount of information than monitoring of atomic molecular units released at a series of individual temperatures over a given time, and also avoids destruction of the wafer being tested. Specifically, while it may be possible to identify some compounds by monitoring the hydrogen, oxygen, water, carbon monoxide, and carbon dioxide released by a wafer as the wafer increases in temperature step-wise, the interaction of these individual components within more complex compounds, and the presence of any complex compounds which are not expected on the wafer makes such analysis highly speculative. In contrast, the rapid temperature excursion and subsequent separation of compounds using the method of the present invention can reliably provide both qualitative and quantitative results.

As described above, once the compounds are released from the wafer, they are collected and pressurized using collection and pressurization systems 6. It should be noted that the present invention is not limited to the single sample container 7 illustrated in FIG. 1, but may also make use of numerous sample containers which are isolatably connected to a common header, or which are individually couplable and uncouplable from the test system. This allows independent optimization of the substrate tests and gas chromatography and/or mass spectroscopy analysis timing, and also allows these individual elements of the present method to be performed at different locations. For example, as a full gas chromatography analysis may require as much as 20 minutes or more to complete, it may be more cost effective to limit such analysis to selected members of a batch of disks, while mass spectroscopy (and/or tandem mass spectroscopy) analysis is performed on more or all of the production disks. Automation of the sample handling system (along with compound analysis, temperature feedback, wafer manipulation, and the like) will generally be handled by the personal computer. Preferably, the sample handling equipment is also fully automated, providing a cassette-to-cassette system for rapid and reliable handling of large numbers of gas samples.

Where identification of unknown contaminants or other compounds is desired, the pressurized sample will generally be injected into a gas chromatograph. The gas chromatograph will preferably be compatible with both electron and chemical ionization techniques. Generally, the gas chromatograph will interface directly with a mass spectrometer 68, so that the gas chromatograph separates the sample into its constituent compounds, while the mass spectrometer scans the separated sample to identify and quantify the individual compounds present. Combined gas chromatography/mass spectroscopy 68 units of bench top size, together with an integrated computer control system, have recently become commercially available. To date, these units have primarily found use only in the biotechnology area. Nonetheless, the volatile organic compounds which often form semi-conductor process contaminants will be identifiable within the mass spectra libraries included in these units.

It is a particular advantage of the system and method of the present invention that the comparison 70 between the mass spectra of the separated compounds and the mass spectra of the library of compounds stored within the computer is fully automated. This allows a semi-technically skilled technician to operate the system, as only a fundamental understanding of chemistry and instrumentation are required. Moreover, where compounds are scanned which do not appear in the commercially available mass spectra libraries, it may be possible to add those compounds to a user defined library. Hence, identification of new compounds should only require more technically skilled intervention a single time, with subsequent identification being provided automatically.

The output of the method of the present invention using a combination of gas chromatography and mass spectroscopy is both qualitative and quantitative 72, with the computer program automatically providing both identification of the compounds present, and their relative amounts within the sample.

When it is desired to identify unknown compounds, or to test large numbers of sample wafers, the system of the present invention can provide tandem mass spectroscopy 74 to search for parent and product ions of a limited number of previously selected compounds. Advantageously, tandem mass spectroscopy can indicate both the presence and quantity of a selected compound without separating the sample. Hence, tandem mass spectroscopy 74 is particularly well adapted for quality assurance of each wafer processed, as it requires less analysis time for each sample as compared to gas chromatography.

Once again, the output from tandem mass spectroscopy is both quantitative and qualitative 76. This allows tandem mass spectroscopy to identify any increasing or decreasing amounts of contaminants within the production stream.

Figure 5A:
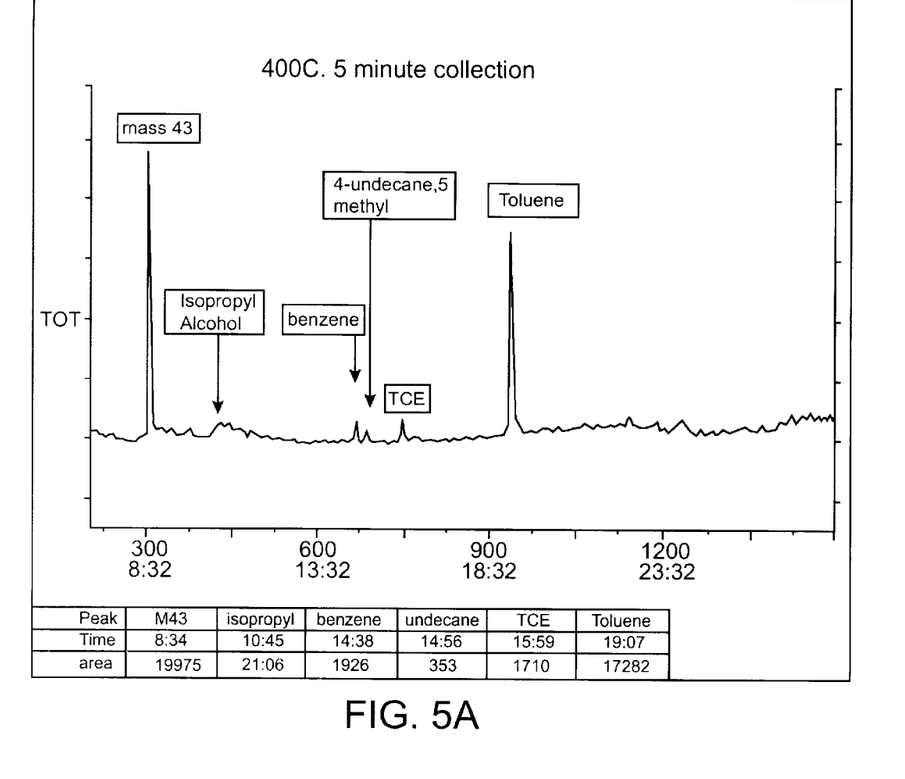
FIGS. 5A–D illustrate typical data provided by the system of FIG. 1, providing both identification and quantification of wafer fabrication contaminants.

The output from the test system and methods of the present invention will be described with reference to FIGS. 5A–D. FIG. 5A illustrates the final output provided by the automated non-destructive test system of the present invention. Advantageously, individual compounds are automatically identified, allowing operators of relatively little training to identify sources of contamination along the production stream.

Figure 5B:
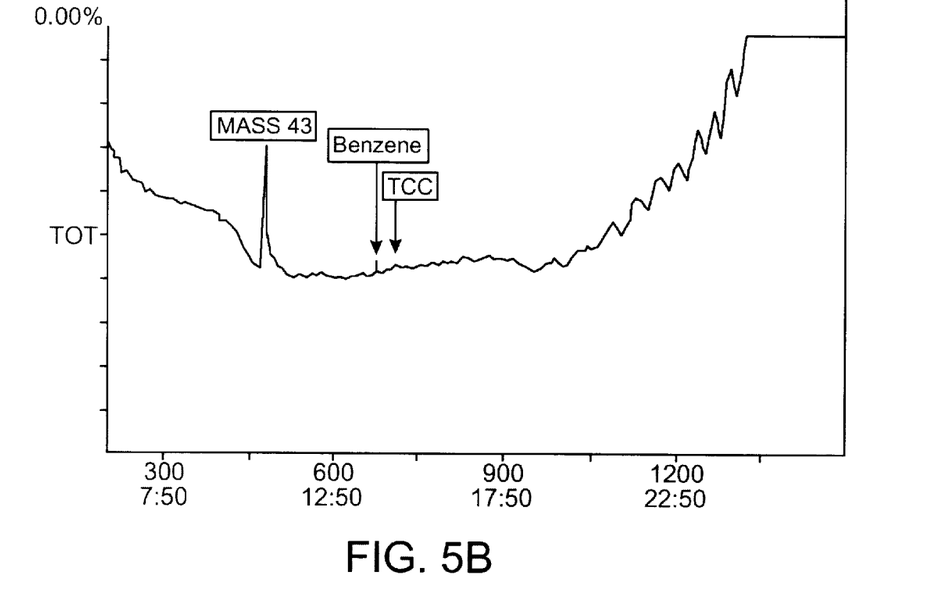
Figure 5C:
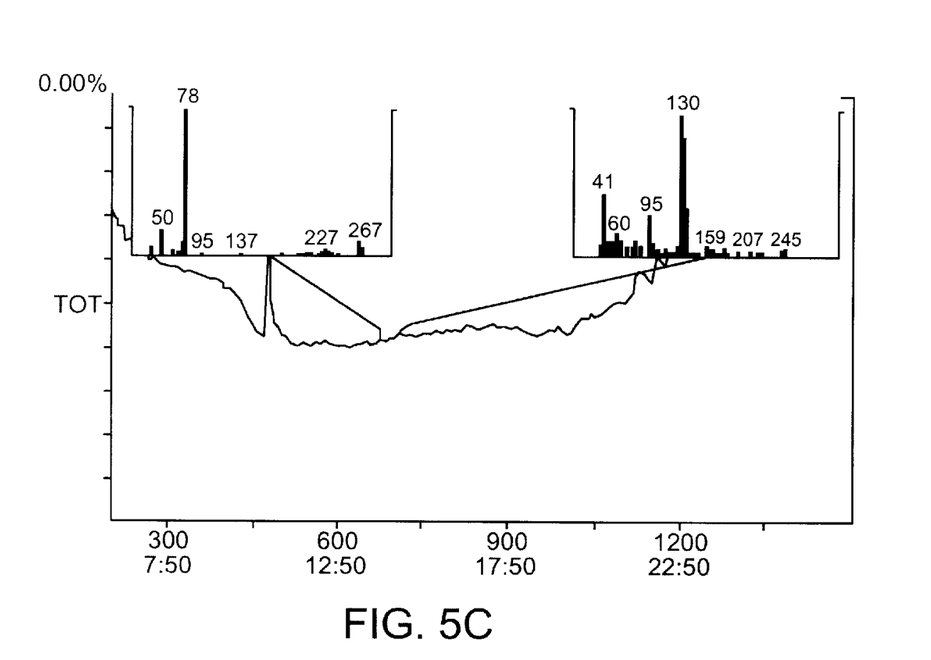

Although such information is not always necessary, the testing system of the present invention is also capable of providing intermediate or raw data to the operator, thereby allowing verification of the results provided. FIG. 5B illustrates a typical chromatograph, with the numbers 300, 600, 900, and 1,200, indicating the individual mass spectrometer scans of the compounds from the sample, while the numbers 7:50, 12:50 . . . indicate the time these compounds were released by the separating column of the gas chromatograph. FIG. 5C illustrates selected mass spectrometer scans superimposed on the chromatogram of FIG. 5B. These individual mass spectrometer scans are the basis for the identification of benzine and trichloroethylene (TCE), which appear on the chromatogram of FIG. 5B.

Figure 5D:
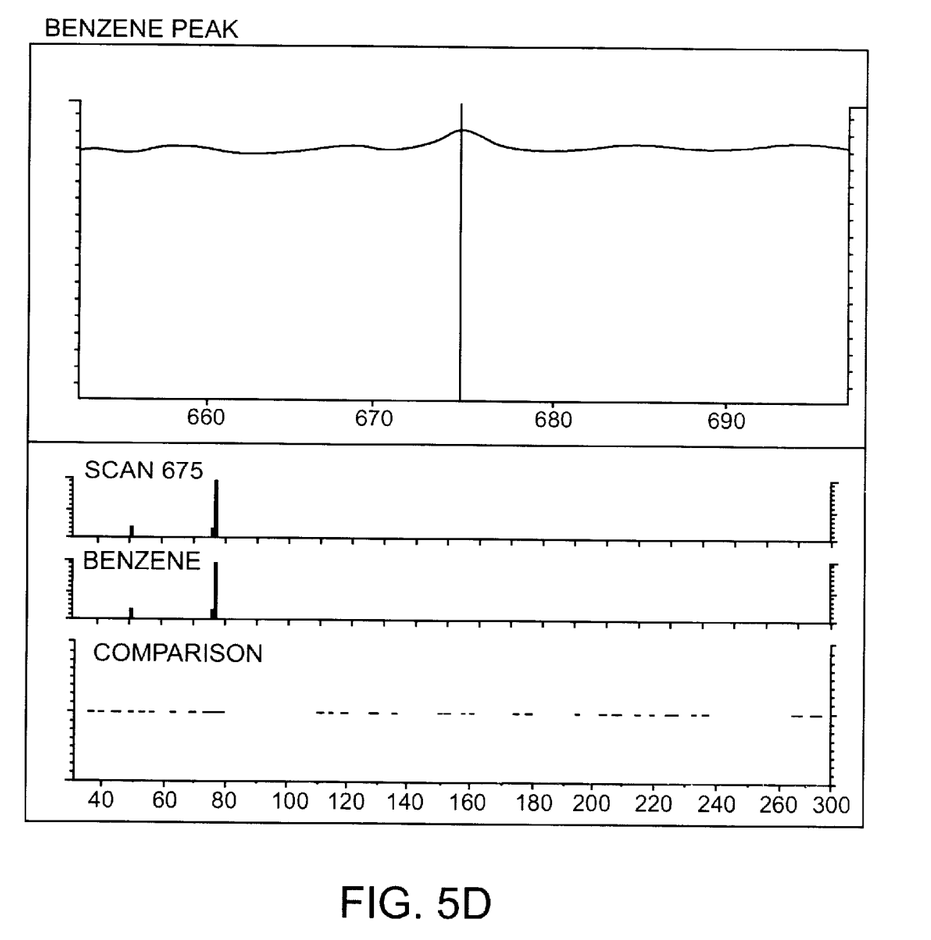

The automated identification of the benzine peak at scan 675 is illustrated in FIG. 5D. The increased output from the separating column during scan 675 is clearly indicated at the top of the figure. The scan itself is compared to known spectra within the library by the computer software, which identifies benzine as having a very similar signature. Clearly, when monitoring such compounds during production, any increase in the amount of benzine which corresponds with an increase in failure rate of the finished wafers would provide a strong indication of the source of the problem, and would greatly facilitate modification of the production processes to reduce or eliminate benzine contamination.

While the exemplary embodiment has been described in some detail, for purposes of understanding and clarity, a variety of modifications, adaptations, and changes will be obvious to those of skill in the art. Therefore, the scope of the present invention is limited solely by the appended claims.

What is claimed is:

1. A method for testing semiconductor wafers, the method comprising:

heating the wafer in an evacuated chamber to release one or more gaseous or particulate chemical compounds from the wafer in a substantially gaseous phase;

cooling the wafer to inhibit diffusion between a plurality of wafer layers and to limit degradation of electrical properties of the wafer;

collecting a gas sample from the evacuated chamber, the sample including the released compounds; and introducing the sample into a gas chromatograph to identify the released compounds.

2. A method as claimed in claim 1, further comprising increasing a pressure of the sample before introducing it into the gas chromatograph.

3. A method as claimed in claim 2, wherein the sample is collected by cryopumping the sample into a low temperature container, and wherein the sample pressure is increased by raising a sample temperature.

4. The system as claimed in claim 1 wherein the contaminant compounds comprise surface contaminants, trapped moisture, or volatile residue compounds.

5. A method for testing semiconductor wafers, the method comprising:

heating the wafer in an evacuated chamber to release one or more compounds from the wafer;

collecting a gas sample from the evacuated chamber, the sample including the released compounds; and introducing the sample into a gas chromatograph to identify the released compounds;

wherein the heating step is terminated prior to substantial diffusion between a plurality of layers of the wafer to avoid degradation of the electrical properties of the wafer.

6. A method as claimed in claim 5, wherein at least a portion of the wafer is rapidly heated to a single predetermined temperature below about 1000° C. to boil the compounds off the wafer, and wherein the wafer cools after a single sample is collected.

7. A method as claimed in claim 5, wherein the heating step comprises direct radiant heating of a target surface of the wafer.

8. A method as claimed in claim 7, wherein the heating step further comprises directing radiant energy onto the target surface while the wafer is suspended within the chamber and while a carrier gas flows over the target surface, the wafer being opaque to the radiant energy and thermally exposed to cooled chamber walls for rapid temperature excursions.

9. A method as claimed in claim 1, wherein the gas chromatograph separates the released compounds, and further comprising comparing mass spectra of the separated compounds relative to a library of compound spectra to identify the released compounds.

10. A method as claimed in claim 9, wherein the gas chromatograph includes an integral mass spectrometer which identifies released compounds and quantifies the amount of released compounds within the sample.

11. A method as claimed in claim 1, further comprising detecting a target compound in the sample with a tandem mass spectrometer.

12. A method as claimed in claim 5 wherein the compounds comprise surface contaminants, trapped moisture, or volatile residue compounds.

13. A non-destructive method for detecting contaminants of semiconductor wafers, the method comprising:

heating at least a portion of the wafer in an evacuated chamber to a target temperature so that one or more contaminant compounds are released by the wafer;

collecting a gas sample from the evacuated chamber, the sample including the released compounds;

terminating heating and cooling the wafer to minimize diffusion between a plurality of layers of the wafer and avoid degradation of the electrical properties across adjacent layers of the wafer;

increasing a pressure of the sample; and introducing the sample into a gas chromatograph or a tandem mass spectrometer to identify the released compounds.

14. A non-destructive test method as claimed in claim 13, wherein the heating step comprises directing radiant energy onto a target surface of the wafer, the target surface of the wafer comprising a material which is opaque to the radiant energy so as to rapidly and directly heat the wafer material.

15. A non-destructive test method as claimed in claim 14, further comprising maintaining a thermal gradient within the wafer from a relatively high temperature adjacent the target surface to a lower temperature opposite the target surface so as to minimize diffusion while heating.

16. A non-destructive test method as claimed in claim 13, further comprising testing each wafer of a plurality of wafers by comparing mass spectra of the released compounds with a plurality of suspect contaminant spectra without separating the compounds in the gas chromatograph, and selecting at least one wafer of the plurality of wafers for gas chromatography to identify unknown contaminant compounds.

17. A non-destructive test method as claimed in claim 13, further comprising storing the sample after collection for subsequent gas chromatography.

18. A quality control system for testing semiconductor wafers for contaminants, the system comprising:

walls defining a vacuum chamber for holding a wafer;

a heat source for raising the temperature of the wafer within the chamber;

a control system coupled to the heat source, the control system limiting heating to prevent diffusion between a plurality of layers of the wafer and limit degradation of electrical properties of the wafer; and a sample collection system which draws a gas sample from within the chamber and passes the sample to a gas chromatograph or a tandem mass spectrometer.

19. A system as claimed in claim 18, wherein the sample collection system increases pressure of the sample from a vacuum within the chamber to inject the sample into the gas chromatograph.

20. A system as claimed in claim 18, wherein the gas collection system comprises a cooled container to draw the sample into the container when the chamber is evacuated, wherein the container is isolatable from the chamber so that raising the temperature of the container increases the pressure of the sample.

21. A system as claimed in claim 18 wherein the walls are cooled such that the wafer is immediately cooled when the heat source is terminated.

22. A system as claimed in claim 18 wherein the heat source is a radiant heat source.

23. A system as claimed in claim 18 wherein the system is adapted to test for the presence of surface contaminants, trapped moisture, or volatile residue compounds.

24. A system for testing semiconductor wafers, the system comprising:

walls defining a vacuum chamber for holding a wafer;

a heat source for raising the temperature of the wafer within the chamber; and a sample collection system which draws a gas sample from within the chamber and passes the sample to a gas chromatograph or a tandem mass spectrometer;

wherein the sample collection system increases pressure of the sample from a vacuum within the chamber to inject the sample into the gas chromatograph;

wherein the heat source comprises a plenum adjacent the chamber and a radiant heater which directs radiant energy through the plenum and onto a target surface of the wafer to directly heat the target surface, wherein a carrier gas is directed over the target surface from the plenum and collected by the sample collection system adjacent a back surface of the wafer opposite the target surface, wherein at least a portion of the walls of the chamber are cooled and the wafer is suspended in the chamber with the back surface of the wafer thermally exposed to the walls so that a thermal gradient within the wafer minimizes diffusion below the target surface, and so that the wafer cools when heating terminates.

25. A method to test wafers for presence of chemical elements or compounds comprising:

placing a wafer in a low pressure chamber that is evacuated by a pumping means;

heating the wafer to release one or more compounds from the wafer, wherein the wafer is heated such that diffusion is controlled and there is limited degradation of the electrical properties of the wafer;

collecting a gas sample from the evacuated chamber, the sample including the released compounds;

introducing the sample into a gas chromatograph; and identifying the released compounds with the gas chromatograph.

26. The method of claim 25 further comprising terminating the heating such that there is no substantial diffusion between a plurality of layers of the wafer.

27. The method of claim 25 further comprising cooling the walls of the low pressure chamber.

28. The method of claim 25 further comprising introducing a carrier to displace atmospheric gas on the wafer.

29. The method of claim 28 further comprising performing a background spectrum analysis to identify and quantify the atmospheric gas on the wafer.

30. The method of claim 29 further comprising increasing the pressure to isolate individual compounds of the atmospheric gas and introducing the atmospheric gas into the gas chromatograph or tandem mass spectrometer.

31. A method for testing a semiconductor wafer for contaminants, the method comprising:

heating the wafer in an evacuated chamber to release one or more contaminant compounds from the wafer;

limiting the heating of the wafer to reduce the diffusion between a plurality of wafer layers and to limit degradation of electrical properties of the wafer;

collecting a gas sample from the evacuated chamber, the sample including the released contaminant compounds; and introducing the sample into a gas chromatograph to identify the released compounds.

32. The method as claimed in claim 31 wherein the released contaminant compounds comprise surface contaminants, trapped moisture, or volatile residue compounds.

* * * * *